United States Patent
Sve et al.

(10) Patent No.: US 6,271,024 B1
(45) Date of Patent: Aug. 7, 2001

(54) COMPARTMENTAL FAST THERMAL CYCLER

(75) Inventors: Charles Sve, Palos Verdes Estates; Pierre Rogelio Valenzuela, Montebello; Timothy Steven Wall, El Segundo; Robert Walter Francis, Manhattan Beach; Robert Bay Pan, Torrance, all of CA (US); Steven John VanWormer, Herndon, VA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 09/250,934

(22) Filed: Feb. 18, 1999

(51) Int. Cl.[7] .................................................. C12M 1/00
(52) U.S. Cl. .................................. 435/303.1; 435/286.1; 435/287.3; 422/104; 422/109; 73/865.6; 374/57; 165/254; 165/258; 165/264
(58) Field of Search ........................................ 422/109, 138, 422/198, 199, 202, 203, 104; 435/287.2, 285.1, 286.1, 287.3, 303.1; 73/865.6; 374/57; 165/253, 254, 258, 264

(56) References Cited

U.S. PATENT DOCUMENTS

| | | | |
|---|---|---|---|
| 5,147,136 | * | 9/1992 | Hartley et al. .......................... 374/57 |
| 5,613,776 | * | 3/1997 | Turner et al. .......................... 374/57 |
| 6,113,262 | * | 9/2000 | Purola et al. .......................... 374/45 |

* cited by examiner

*Primary Examiner*—David A. Redding
(74) *Attorney, Agent, or Firm*—Derrick Michael Reid

(57) ABSTRACT

A fast thermal cycler has a temperature chamber divided into a top, hot compartment heated by heating lamps and a bottom cold compartment cooled by liquid nitrogen, for optimizing thermal cycling rates for devices under test, such as solar cells, for rapid thermal life testing where both compartments use pressurized gaseous nitrogen for thermal conduction and regulation and a motor drive repetitively transports a test device mounted on a panel transiting between the two compartments. The thermal cycler is enhanced by computer control, enabling in-situ electrical testing, fail-safe heating, precision temperature heating and cooling phases, operator alerting and thermal gradient control during the temperature cycling.

12 Claims, 5 Drawing Sheets

THERMAL CYCLING SYSTEM

THERMAL CYCLING SYSTEM

FAIL SAFE MOTOR CONTROL

CURRENT TEST CONTROL

RESPONSE CONTROL

COMPARTMENTAL FAST THERMAL CYCLER

STATEMENT OF GOVERNMENT INTEREST

The invention was made with Government support under Contract No. F04701-93-C-0094 by the Department of the Air Force. The Government has certain rights in the invention.

FIELD OF THE INVENTION

The invention relates to the field of thermal cycling and thermal cyclers for temperature testing of devices and components such as solar cells and microelectronics.

BACKGROUND OF THE INVENTION

Thermal cyclers have long been used to repetitively heat and cool devices over wide temperature ranges to validate device designs. In the past, the design validation process has been the most prevalent bottleneck encountered in the development of new solar cell designs for critical mission applications. The customer demand to acquire desired thermal cycles before an urgent launch deadline requires accelerated cycling rates for a thermal cycling validation.

Various types of thermal cyclers have been used to perform the thermal cycling validation and testing process. One example is a conductive thermal cycler that has been used to perform life tests on GaAs solar cells. Cycling is achieved by cooling a fairly massive aluminum plate with counter-flowing liquid nitrogen and then heating the plate with symmetrically embedded electric rod-heaters. The devices under test are held in contact with the plate so that cycling occurs primarily by conduction. Typical solar cells mounted on lightweight ¼ inch thick honeycomb panels generally require sixty to ninety minutes to cycle between +80° C. and −80° C. while under 1X10E-7 Torr vacuum. The conductive cycler is well suited for vacuum cycling of cells mounted on heavy ⅛ inch thick solid aluminum panels. However, the conductive thermal cycler has poor cycling rates, because the heat and cool phases work against each other in driving the conductive plate to hot and cold temperatures.

Another type of thermal cycler that has been used is the radiant thermal cycler. In the radiant thermal cycler, quartz-halogen lamp radiation is used in a vacuum with a surrounding cold shroud for heat absorption to cycle the cells, as opposed to the direct conduction method employed by the conductive thermal cycler. A shroud is a cooled copper cylinder surrounding the test device and heating lamps inside the vacuum chamber. Cycle periods of thirty to sixty minutes are attainable on lightweight ¼ inch thick honeycomb panels. Radiant thermal cyclers are well suited for vacuum cycling thin, lightweight specimens with large surface areas. These radiant cyclers have a faster cycling rate than conductive cyclers because only the heat phase works against the cool phase when the heating lamps overcome the cooling shroud effects. The shroud can only recover during the next cool phase even though the shroud is being filled with liquid nitrogen during the heat phase.

Recently, an improved method was used for optimizing the cooling rate for the radiant thermal cycler with the introduction of a small amount of nitrogen gas inside the vacuum chamber so that the conduction of heat from the solar cell coupon under test to the cold shroud is assisted by the nitrogen gas. This nitrogen-assisted cooling is done without a significant degradation of the radiant cooling contribution. The result is a net increase in the cooling rate. It has been experimentally demonstrated that a significant improvement in the cooling late was achieved by maintaining a forty mTorr nitrogen pressure during the cool phase. This pressure yielded shorter cycle periods of twenty-two to forty-five minutes on lightweight ¼ inch thick honeycomb panels. Under nitrogen gas cooling, the disadvantages remain that the heat phase still works against the cool phase, and only panels of very low mass can be cycled rapidly.

Usually, a single chamber has to be repetitively heated and cooled requiring excessive energy and cyclic time depending on the amount of mass being thermally driven. The required time-consuming thermal cyclic tests are needed to qualify solar cells and other components particularly for space applications. In order to validate solar cell panel designs in a more timely manner, faster thermal cyclers are desirable. With the above designs, thermal life testing of devices could last for as long as several years for 50,000 cycles. Also, during heating and cooling phases, undesirable thermal gradients may be created across the device under test. A common solution in the thermal cycling industry is to ignore this problem by using only one control thermocouple positioned in the middle of the test device for customer data logging. These and other disadvantages are solved or reduced using the present invention.

SUMMARY OF THE INVENTION

An object of the invention is to provide fast thermal cycling testing of devices.

Another object of the invention is to provide hot and cold compartments within a thermal cycling chamber to provide fast thermal cycling testing of devices.

Another object of the invention is to provide individually controlled multiple heating elements and temperature sensors for reducing thermal gradients experienced by a device under test.

Still another object of the invention is to provide in-situ electrical testing of the device under test.

The invention is directed to a fast thermal cycling system. A test device, such as a solar cell array coupon, is attached to a panel and placed in a temperature cycling chamber. The temperature cycling chamber has a top hot compartment and bottom cold compartment creating a temperature gradient from a top hot compartment heated by a heater means to a bottom cold compartment cooled by a cooler means. The chamber is filled and pressurized with an ultrapure gas, such as nitrogen, for thermal conduction within the compartments. The panel is repetitively transported between the hot top compartment and the bottom cold compartment for rapid thermal cycling of the device under test. The chamber is constantly pressurized by the gas to slightly above ambient atmospheric pressure, with the gas being vented out the top of the chamber by adjustable vent valves. A motor-pulley system raises and lowers the test device during testing along a vertical track joining the two compartments. The entire chamber is insulated and these two compartments are thermally isolated from one another, except for an opening between the compartments, through which the panel and test device are mechanically cycled.

There are several advantages of the dual compartment thermal cycler invention. The cool phase and heat phase no longer work against each other. Heating lamps keep the top compartment hot, and a cold liquid fluid, such as liquid nitrogen, keeps the bottom compartment cold. The temperature in both compartments is kept stable by gas thermal conduction. One compartment is able to fully recover to its operating temperature while the other compartment is actively heating or cooling the panel and test device. The chamber is large enough to accommodate thick curved fiberglass panels with an aluminum honeycomb filler.

The primary feature of the cycler is the dual compartment chamber for separate heating and cooling phases. Heating lamps, such as quartz-halogen infrared heating lamps, are located in the top hot compartment. These lamps surround the panel during the heat phase and maintain the top hot compartment at an elevated temperature, so that the panel is warmed both by radiation and by gaseous conduction. The panel is lowered into the bottom cold compartment for the cool phase where the surrounding walls are maintained at extremely low temperatures by the cold liquid fluid in an outer container. The panel is cooled both by radiation from the cold walls and by gaseous conduction. The top compartment is maintained at a high temperature during the cool phase, while the bottom compartment is maintained at a low temperature during the heat phase. In this manner, neither compartment expends any time recovering to a respective original operating temperature during use. Exceedingly fast thermal test cycles are practical. These cycles take approximately five to ten minutes. A computer is utilized to control the motor transportation, lamp heating, gas conduction, cold liquid fluid flows, and temperatures.

An in-situ testing feature of the cycler can be used to eliminate needless testing of a device that may have failed electrically. The cycler tests the devices for electrical failures by periodically performing in-situ electrical tests on the device being tested. For solar cells, an in-situ current test and bypass diode test are incorporated into the thermal cycler to determine if the solar cells remain functional during cycling. The solar cells do not have to be removed during thermal cycling, but are rather tested in-situ.

A fail-safe feature is used to protect the test device from excessive heat or cold. Part of this fail-safe feature is a counterweight attached to the motor. This motor raises and lowers the panel and attached test device, as needed, between the two compartments of the chamber. If the motor loses power, the counterweight raises the panel and test device into the upper hot chamber, where a variac provides power to the lamps to keep the device warm. The fail-safe feature is particularly desirable during tests that run continuously for months. If there is a motor power loss, the computer can be used to notify the user.

A thermal gradient control feature controls the temperature gradient across the test device. These gradients are controlled through sensing thermocouples strategically placed across the test device. The temperature gradient across the test device in the bottom compartment is minimized by the bottom heat lamp, gas mixing vents, and vertical positioning of the test device. The. computer controls the motor to vertically position the test device within the bottom compartment for improved repeatability of the cooling temperatures. The computer is also used to control the temperature gradients in the upper compartment during the heating phase by controlling the heat generated by the heating lamps. These and other advantages will become more apparent from the following detailed discussion of the preferred embodiment.

DETAILED DESCRIPTION OF THE PREFERRED EMBODIMENT

Figure 1:
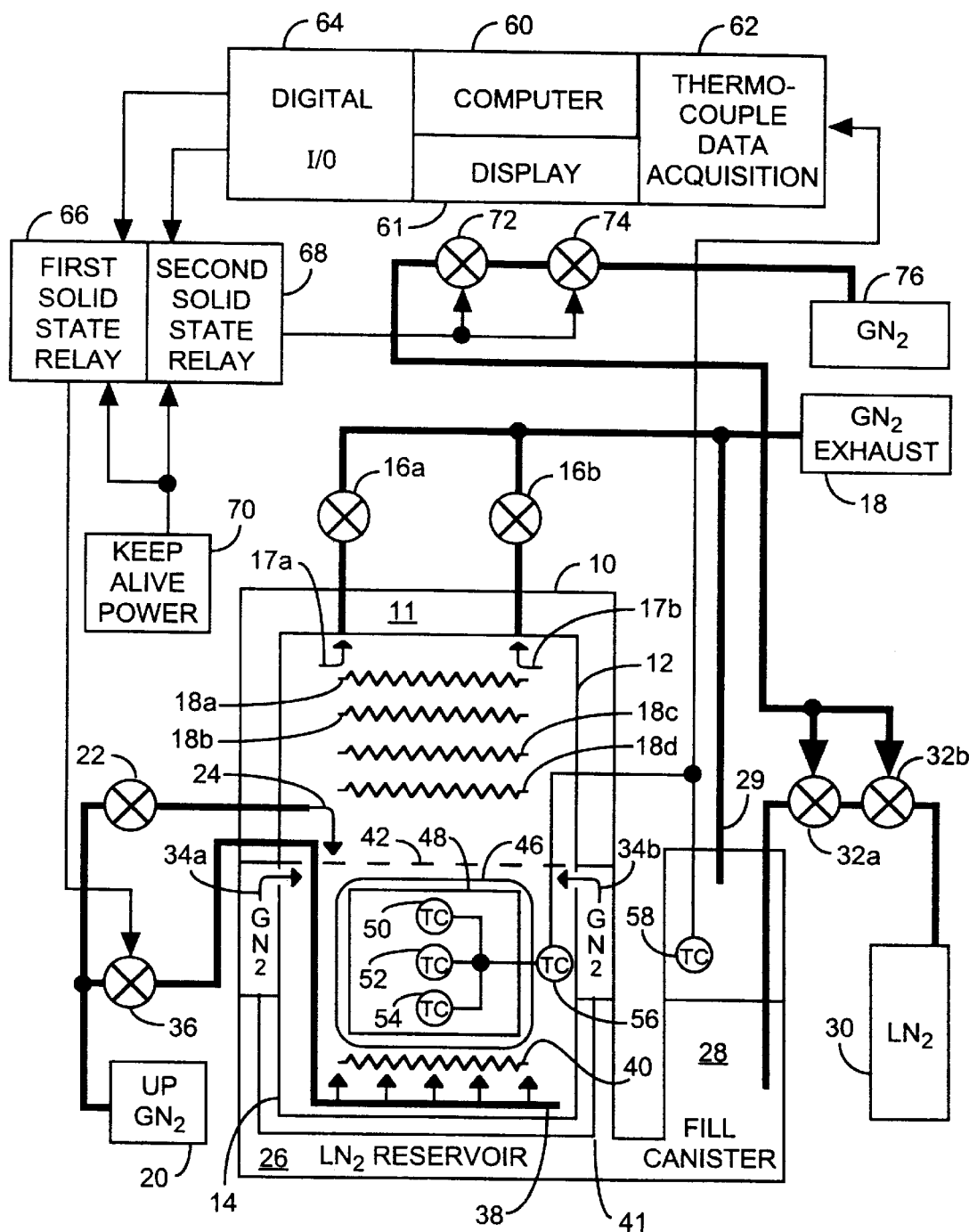
FIG. 1 is a diagram of a temperature cycling chamber.

An embodiment of the invention is described with reference to the figures using reference designations as shown in the figures. Referring to FIG. 1, a temperature cycling system includes a chamber 10 having suitable insulation 11, a top hot compartment 12 and a bottom cold compartment 14. The top compartment 12 has two manual top venting valves 16a and 16b for venting gaseous nitrogen through respective top vents 17a and 17b to a gaseous nitrogen exhaust 18. The top hot compartment 12 is heated by four sets of heating lamps 18a, 18b, 18c and 18d. An ultrapure gaseous nitrogen source 20 supplies gaseous nitrogen to a manual meter valve 22 venting gas through a top purge vent 24 for purging the gas through the top compartment 12. The bottom compartment 14 is cooled by a liquid nitrogen reservoir 26 receiving the liquid nitrogen from a fill canister 28 that in turn receives the liquid nitrogen from a liquid nitrogen source 30 through two gas operated liquid nitrogen bellows valves 32a and 32b. The insulation 11 preferably extends around both compartments 12 and 14, reservoir 26, and fill canister 28. Gaseous nitrogen from liquid nitrogen in the reservoir 26 flows into the bottom cold compartment 14 through bottom vents 34a and 34b. A solenoid valve 36 is used to provide the nitrogen gas through a bottom purge venting manifold 38 during cooling in lower compartment 14. The bottom cold compartment 14 can be heated by a bottom heater 40. A mounting panel 46 mounting a device under test 48 is shown by example in the bottom compartment 14. Thermocouples 50, 52, 54 are positioned on the device 48 to sense the temperature across the device 48. Thermocouple 56 is preferably placed on the shroud 41 for measuring the temperature of the shroud 41 and hence to measures the temperature of the bottom compartment 14. The thermocouple 58 is placed in the fill canister 28 for measuring the temperature to determine the level of the liquid nitrogen in the canister 28.

A computer 60 having a display 61 is used to control the operation of the thermal cycling system. The computer controls the movement of the panel 46 that transits between the top and bottom compartments 12 and 14. The computer 60 has thermocouple data acquisition ports 62 for receiving temperature signals from the thermocouples 50, 52, 54, 56 and 58. The computer 60 also has digital I/O ports 64 for controlling a first solid state relay 66 and a second solid state relay 68 both connected to keep alive power 70 to supply power through the relays 66 and 68. Cold nitrogen gas tends to settle at the bottom of the lower compartment 14. Relay 66 controls solenoid valve 36 for mixing the nitrogen during cooling in lower compartment 14 by conducting gaseous nitrogen from an ultrapure gaseous nitrogen source 20. A gaseous nitrogen source 76 supplies gaseous nitrogen to the valves 72 and 74. The valves 72 and 74 are used to control liquid nitrogen bellows valves 32a and 32b for supplying liquid nitrogen from the liquid nitrogen source 30 to the fill canister 28.

The computer 60 is used to control the thermal cycling of the device 48 with a rapid cycle period, for example, of less than five minutes. The panel 46 is moved through the aperture 42 into the lower compartment 14 at the beginning of a cooling phase and is moved through the aperture 42 into the upper compartment 12 during a heating phase. The panel 46 is moved repetitively between the top and bottom compartments 12 and 14 during repetitive heating and cooling phases to thermal cycle the device 48 under thermal cycling tests. The thermal cycling system achieves fast cycling rates with an optional dwell time in the top compartment during the heating phase. A typical cycle profile for a panel 46 may have a small dwell time and an increased cycle time in order to avoid exceeding specific panel and device thermal rate limits. A typical complete cycle consists of a heat phase, a heating-dwell phase, and a cool phase.

The heat phase preferably employs four sets of two stationary quartz-halogen infrared lamps used as heaters 18a–d positioned horizontally on either side of the panel 46 when moved into the top compartment 12. The thermocouples 50, 52 and 54 are mounted on the panel so that thermocouple 50 is directly in line with the first set of lamps 18a at the top, thermocouple 52 is between the two middle sets of lamps 18b and 18c, and thermocouple 54 is directly in line with the last set of lamps 18d at the bottom of the top compartment 12, when the panel 46 is suspended in a proper heating phase position in the top compartment 12. The three thermocouples 50, 52 and 54 together with the lamp currents, provide feedback for thermal control. The normal resting position for the panel is between the lamp sets 18a–d in the top compartment 12 during the heating phase in the heating position.

To perform liquid nitrogen fills, the computer 60 outputs a digital logic level from the digital I/O 64 to energize the second solid-state relay 68. This relay 68 in turn energizes redundant solenoid valves 72 and 74 passing gas to the redundant bellows valves 32a and 32b. The valves 72 and 74 are redundant to ensure that the nitrogen gas is turned off. The nitrogen gas then actuates the liquid nitrogen bellows valves 32a and 32b, allowing liquid to enter the fill canister 28 and the reservoir to cool the shroud 41 so as to cool the interior of the bottom compartment 14. The two solenoid valves 72 and 74 and the two bellows valves 32a and 32b are redundantly used during the liquid nitrogen fills to prevent fill runaway in case any one of the valves fails to operate. The thermocouple 58 may be placed on a probe to hold the thermocouple 58 in the fill canister 28 to measure the temperature of the fill canister 28 to determine the fill level of the liquid nitrogen in the fill canister for feedback to the computer 60. Another thermocouple, 56, is placed on the shroud 41 to measure the temperature of the shroud to provide additional feedback to the computer 60. As the liquid nitrogen gasifies, the gas is routed through strategically placed vents 34a and 34b located near the top of the bottom cooling chamber. A vent 29 is used to pass gaseous nitrogen from the fill canister 28 to the exhaust 18 to prevent over pressurization of the fill canister 28. The cold gas in the cold compartment 14 and the cold walls of the shroud 41 function to cool the panel 46 by thermal conduction, convection and radiation.

To turn on the nitrogen purge, solenoid valve 36 is energized, allowing ultrapure gaseous nitrogen to be distributed uniformly from the manifold 38 mounted in the bottom of the cooling compartment 14. This purging maintains a homogeneous thermal mixture and slightly pressurizes the chamber 10 to keep moist air out. The lamp 40 positioned just below the panel 46 is used to compensate for thermal gradients across the panel 46. In the event of a loss of keep-alive power 70 due to a hardware triggered failure or software triggered failure, power is removed from both solid-state relays 66 and 68 so that the gaseous nitrogen purge and liquid nitrogen fill are immediately disabled.

Figure 2:
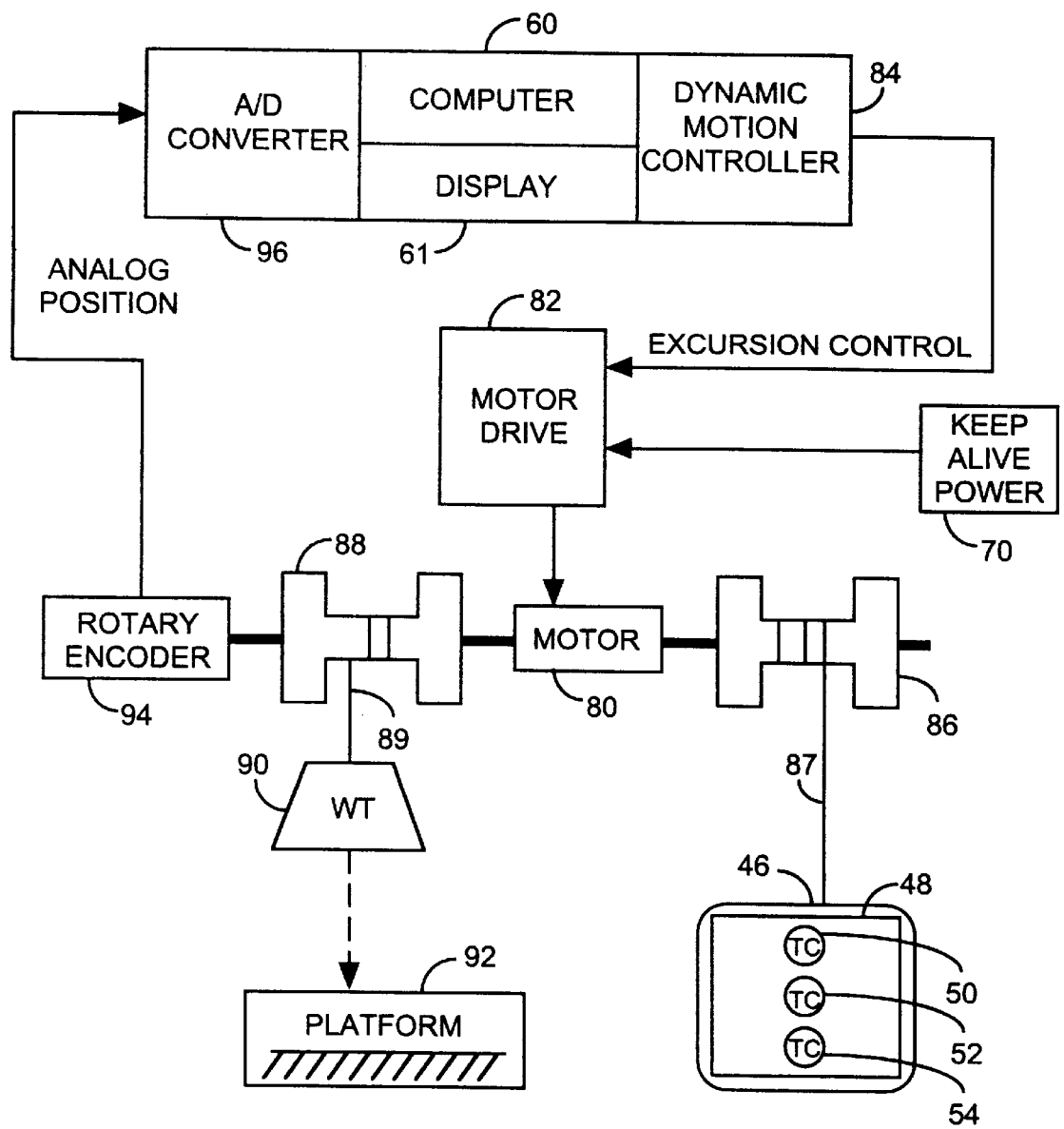
FIG. 2 is a diagram depicting microstepping motor control.

Referring to FIGS. 1 and 2, anytime that power or control for the thermal cycling system is interrupted, a fail-safe motor control procedure is activated. A motor 80 is controlled by a motor drive 82 that is in turn controlled by a dynamic motion controller 84 and powered by the keep alive power 70. During thermal cycling, an excursion control signal from the controller 84 is used to control the movement of the panel 46. The motor 80 simultaneously rotates a first pulley 86 connected by a cable 87 to the panel 46 and rotates a second pulley 88 connected by a cable 89 to a counterweight 90 that can drop under gravity to a platform 92. A rotary encoder 94 provides an analog position signal to an analog to digital converter 96 for feedback control of the movement of the panel 46. Motor microstepping is controlled by the computer. The computer 60 issues motor excursion commands to the motor driver 82 using a dynamic motion control card that controls the motor driver 82. A rotary encoder 94 provides position feedback information, which the computer 60 compares with the motor pulse counts for agreement. As the panel 46 is lowered into the bottom cooling chamber with the panel excursion pulley 86, the counterweight 90 is raised off a platform 92 with counterweight pulley 88. The panel excursion 86 pulley moves the panel 46 between the two compartments 12 and 14. When the counterweight 90 sits on the platform 92, the panel 46 is at the home position between the lamps 18a–d in the upper heating chamber 12. Any software-triggered failures or hardware faults result in immediate thermal cycling termination. When keep alive power 70 to the motor drive drops, the counterweight 90 pulls the panel 46 back up into the home position, where low lamp power keeps the panel 46 warm. During a power interruption that drops power to the motor 80, the counterweight 90 pulls by gravity the panel 46 up into this safe home position, and the lamps keep the panel warm for example at 40° C. with low variac power 98 supplied from an uninterruptable power supply 99 shown in FIG. 3.

Figure 3:
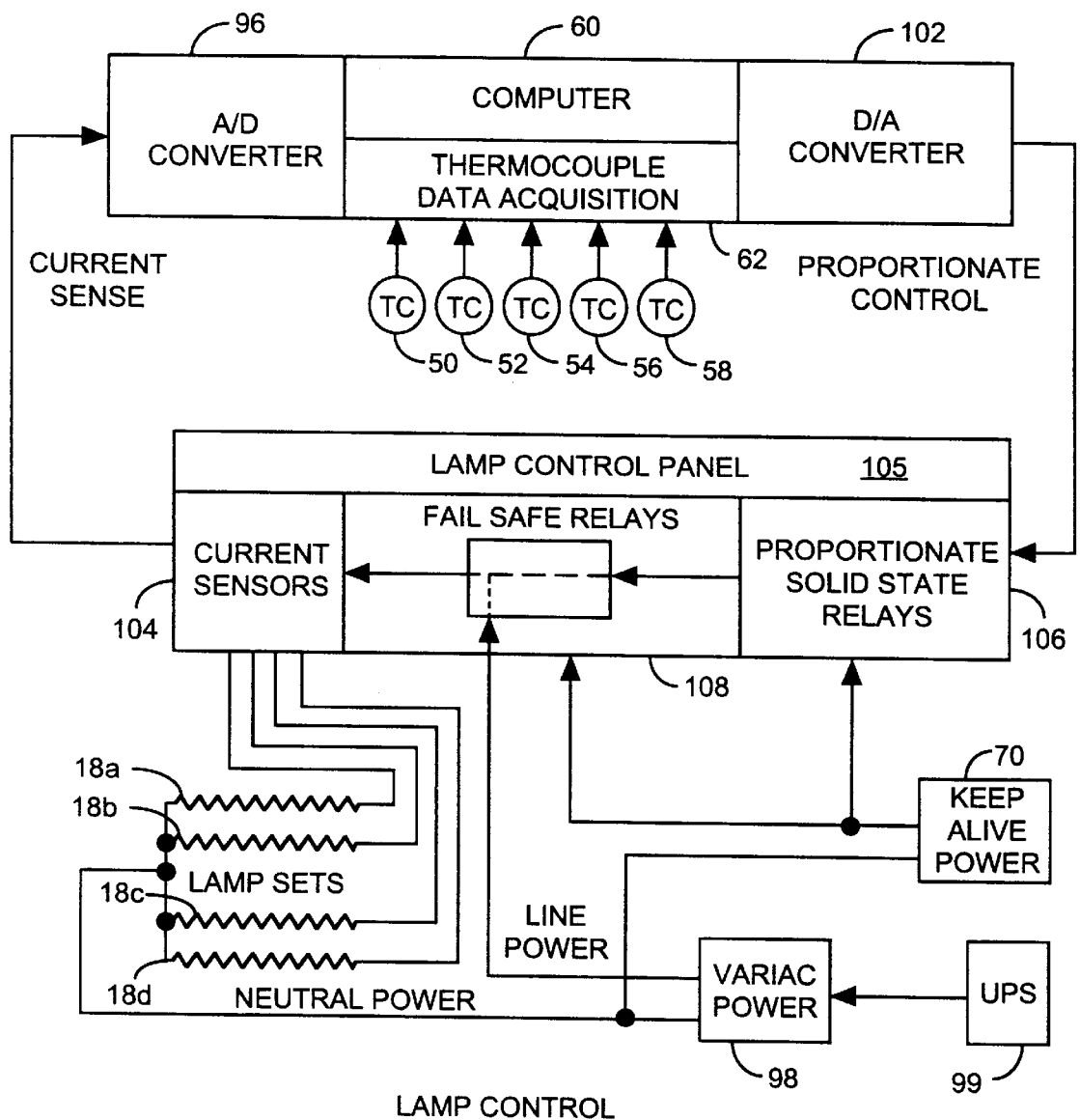
FIG. 3 is a diagram depicting lamp control.

Referring to FIGS. 1, 2 and 3, a lamp control process is used for controlling the current through each of the heater lamp sets 18a–d. The computer 60 having the analog to digital converter 96 further includes a digital to analog converter 102 for controlling current through a given lamp set 18a–d, using a, lamp control panel 105 having four respective lamp current sensors 104 for sensing lamp current and providing four respective analog current sense signals to the A/D converter 9G, and having four respective proportionate solid state relays 106S for receiving four respective analog proportionate control signals from the D/A converter 102 for controlling the power to the lamp sets 18a–d. The lamp control panel 105 further has four fail safe relays 108 for providing proportionate power from the keep alive power 70 to lamp sets 18a–d during normal cycling and provides variac power 98 from the uninterruptable power supply 99 during power or control interruptions of the thermal cycling process. Upon entry of the panel 46 into each new heating phase, the four lamp sets 18a–d are first equalized to a preset current that determines the maximum heating rate for the entire heating phase. During the heating phase, the lamp currents for the two midlamp sets 18b and 18c are linearly ramped up to a second current level in proportion to the midpanel temperature, reaching the maximum current at the heating extreme. At the same time, power for the top and bottom lamp sets 18a and 18d is proportionately controlled as a function of the difference between each top and bottom thermocouples 50 and 54 and the midcontrol thermocouple 52. This control of power ensures that the top and bottom panel temperatures are slaved to track the midcontrol temperature sensed by the thermocouple 52. In this manner, the panel temperatures increase together to a target temperature with no thermal gradients across the panel when in the upper compartment 12 and with excellent repeatability.

The computer 60 outputs the proportionate control voltage signals from the D/A converter 102 to vary the proportionate solid-state relays 106 that provide controllable lamp power to lamp sets 18a–d. The proportionate solid-state relays 106 provide power to lamp sets 18a–d under computer feedback control using the sensed current through the lamp sets and the set of lamp thermocouples 50, 52, and 54 on the panel 46. In the event of a loss of keep-alive power due to a hardware triggered failure or software triggered failure, keep alive power is removed from the lamps 18a–d to prevent thermal runaway, and lamp power is supplied by a back-up variac 98. The variac 98 is powered by a uninterruptable power supply 99 and is set to a very low output to ensure that the panel is kept warm to approximately 40° C. to prevent thermal runaway.

In actual operation, the thermal inertia of the panel 46 arising from accelerated heating rates can result in excessive overshoots at the heating extreme that could lead to damage of the device 48, such as sensitive solar cells 48. To avoid these thermal overshoots, the temperature control converges toward a variable temperature target below the desired temperature extreme by evaluating a heating time profile experience during the last heating phase and the control adjusts the target accordingly to prevent an overshoot. This overshoot control method continually corrects for any changes in ambient temperature or for other influences that affect thermal overshoots or undershoots. In addition, this overshoot control method ensures that the temperature cycles will tend to consistently meet a desired temperature extreme. When the midcontrol thermocouple 52 reaches this variable target temperature extreme, a heating dwell phase is initiated.

In the heating-dwell phase, the panel 46 remains in the home position between the infrared lamps 18a–d in the top compartment 12 where the lamps 18a–d maintain the panel 46 at the heat phase extreme. It is common to set a dwell time period during the heating phase. A thermal soaking period at the heating extreme ensures that the entire panel 46 reaches a constant temperature free from gradients. The dwell period can also emulate actual conditions the device is expected to experience in a given application. Because the dwell phase holds the panel 46 at the most constant temperature in the cycle, the dwell period can also be used to perform any electrical tests on the panel 46 that might be temperature dependent.

Cooling is accomplished in the bottom compartment using the surrounding shroud 41 maintained at –188° C. by filling reservoir with liquid nitrogen from the fill canister 28. As the liquid nitrogen in the reservoir 26 gasifies, this gas is directed into the cooling compartment through vents 34a and 34b strategically placed along the top of the bottom compartment 14. The very cold, dry nitrogen gas is comparatively heavy in the bottom compartment 14, and so gas tends to flow down towards the bottom cooling compartment 14 to surround the panel 46 and hence the device under test 48. Thus, the panel 46 is not in direct contact with liquid nitrogen. An external gaseous nitrogen purge through valve 36 and manifold 38 is also introduced into the bottom of the bottom compartment 14 during the cool phase to promote a more homogeneous thermal mixture. This purge through the manifold 38 is used in addition to the constant chamber pressurizing purge through valve 22 and vent 24 delivering gas into the upper compartment 12.

The device under test 48 is instrumented with the three control thermocouples 50, 52 and 54. Redundant thermocouples, not shown, may be used as spares for redundancy and corroboration. For example, a control and a spare thermocouple may be located at the top edge, at the bottom edge, and at the exact middle of the panel, respectively. Due to thermal edge-effects, the panel will always tend to get colder more quickly along its bottom and top edges than in the middle during the cooling phase. This tendency creates thermal gradients across the panel 46. To compensate for these thermal gradient effects along the bottom edge of the panel, the stationary infrared lamp 40 in the bottom of the cooling compartment 14 is energized during the cooling phase. The edge-effect is countered at the top edge by how far the panel 46 is allowed to travel into the cooling compartment. The thermal gradients can increase dramatically with accelerated cycling rates, and the use of the thermocouples 50, 52 and 54 along with heating by lamp 40 and gas purges through manifold 38 can be used to decrease the thermal gradients during the cooling phase.

At the end of the heat-dwell phase, the bottom edge-effect cool lamp 40 is energized, the nitrogen mixing begins, and the motor 80 transports the panel 46 from the home position in the top compartment 12 to a predetermined home position in the bottom compartment 14 where cooling begins. The panel 46 is cooled by the cold nitrogen gas and by radiation to the surrounding cold shroud 41. Both the cool-lamp current that heats the bottom edge of the panel 46 and the panel excursion position indicating the top edge are programmed to converge the temperature values such that both the top and bottom panel temperatures equal the midpanel temperature at the instant the midpanel reaches the cooling target extreme. Because these temperature values are determined by the results of the preceding cycle, the computer 60 constantly compensates for slowly changing environmental influences.

Similar to the heat phase, the accelerated cooling rates can result in the panel dropping significantly below and undershooting the cool target extreme at the transition from cooling to heating. This undershoot tendency is corrected by programming control to converge the temperature towards a variable dynamic temperature target above the desired extreme. The temperature target is determined by evaluating the preceding cycle temperature performance and adjusting the target temperature accordingly, thereby continually correcting for influences affecting this transition. When the midcontrol thermocouple reaches this variable target extreme, the cool lamp and nitrogen purge are turned off, and the panel is transported back to the home position in the top compartment, where the heat phase is re-initiated and the next thermal cycle begins.

Figure 4:
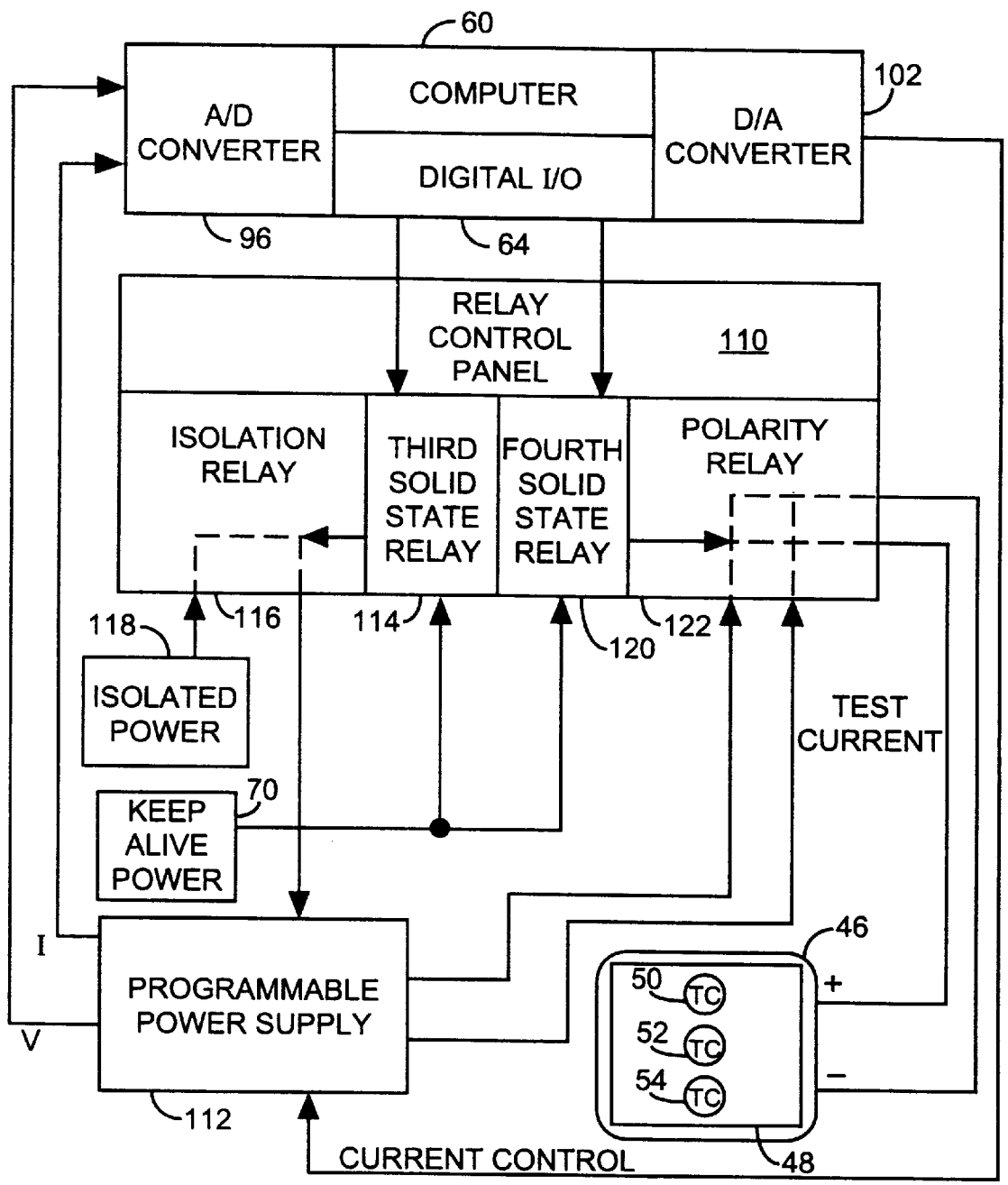
FIG. 4 is a diagram depicting current test control.

Referring to FIGS. 1 through 4, and particularly to FIG. 4, the thermal cycling system can be enhanced to provide a capability for electrically testing the device 48 in response to additional cycling testing requirements. Because the panel 46 might be removed for elaborate performance evaluations only after thousands of cycles or more, it is desirable to verify that the device 48 is still functional without interrupting temperature cycling or removing the panel 46 from the thermal cycling system. Therefore, the thermal cycling system preferably includes a method that performs fully automated in-situ electrical performance tests. In the case of solar cells 48, conventional bypass diode tests and current tests can be performed alternately any number of predetermined cycles, such as every ten cycles. In the case of solar cell devices 48, predetermined current levels are injected into the solar cell circuits 46 and the corresponding voltages produced across the cells are measured. Because these measurements are panel temperature dependent, the measurements are preferably taken during the dwell phase. These solar cell performance and interconnect integrity checks provide indicators to allow for immediate termination of the thermal cycling in the event of cell degradation or failure. These indicators promote the discovery of failure mechanisms, contribute to more accurate panel survival data, and save qualification time by terminating the cycling of damaged cells.

The computer 60 uses a relay control panel 110 and a programmable power supply 112 to conduct test current through the devices 48 on the panel 46. The relay control panel 110 includes a third solid state relay 114 connected to an isolation relay 116 that is in turn connected to an isolated power source 118, and includes a fourth solid state relay 120 connected to a polarity relay 122. Both of the third and fourth relays are connected to keep alive power 70 and are controlled by control signals from the digital I/O 64 of the computer 60. The solid state relays 114 and 120 pass 115 VAC when triggered by the control signals from the digital I/O 64. The keep alive power 70 is present when no failures have occurred. The polarity relay is used for reversing the polarity of the test current to the devices 48. The programmable power supply 112 provides the test current and communicates voltage levels of the device 48 to the A/D converter 96 of the computer 60 for sensing the voltage on the devices 48 during current testing. A DC analog control current signal determines the level of current provided by the programmable constant current power supply 112. Isolated instrumentation power source 118 is derived from the 3.0 KVA uninterruptable power source 99.

The in-situ current and bypass diode tests are performed at the top of the thermal dwell phase as often as desired. The computer 60 can be programmed to provide menu-selectable options for initiating and monitoring the in-situ tests. The two in-situ tests are identical, except for the direction of current flow and the resulting voltages produced across the solar cells that are preferably connected in a series. The test begins by energizing or de-energizing a fourth relay 120 to control the polarity relay 122 for setting the desired current flow direction using a controlling logic signal from the digital I/O 64 that triggers the relays 120 and 122. The programmable constant current power supply 112 outputs the test current in proportion to an analog input voltage from D/A converter 102 as a current control signal and supply 112 then provides analog output voltage V representing the voltage across the device 48 and an analog output voltage I representing the current through the device 48. These voltages V and I are communicated to the A/D converter 96 to provide feedback for closed-loop control of the test current from the programmable constant current power supply 112 using the current control signal from the D/A converter 102. A dwell time period of a minute is usually long enough to perform an electrical test during the dwell phase. The first thirty seconds allows the panel 46 to come to thermal equilibrium. Then a programmable current source power supply 112 linearly ramps the test current through the solar cells of device 48 up to a predetermined level, such as 0.200 amps, in ten seconds, and holds the current constant for another ten seconds. The computer 60 generates a ramped voltage output from the D/A converter as the current control signal, that controls the programmable constant current power supply to ramp up the test current to the desired 0.200 amp level in ten seconds, where this test current level is then held for a predetermined amount of time, for example, ten seconds. At this time, the voltage across and the current through the cells 10 are measured and archived by the computer 60. Then the test current is ramped back down to zero in another ten seconds, completing the test. Loss of keep alive power, or a software triggered failure will both result in the programmable constant current power supply being powered down to protect the solar cells 48 from current runaway. Both the current and the bypass diode tests are identical, except for the direction of the applied test current. Once the remainder of the dwell time has expired, the motor 80 transports the panel 46 from the home position in the top compartment 12 to a predetermined home position in the bottom compartment 14, where the cool phase begins.

Figure 5:
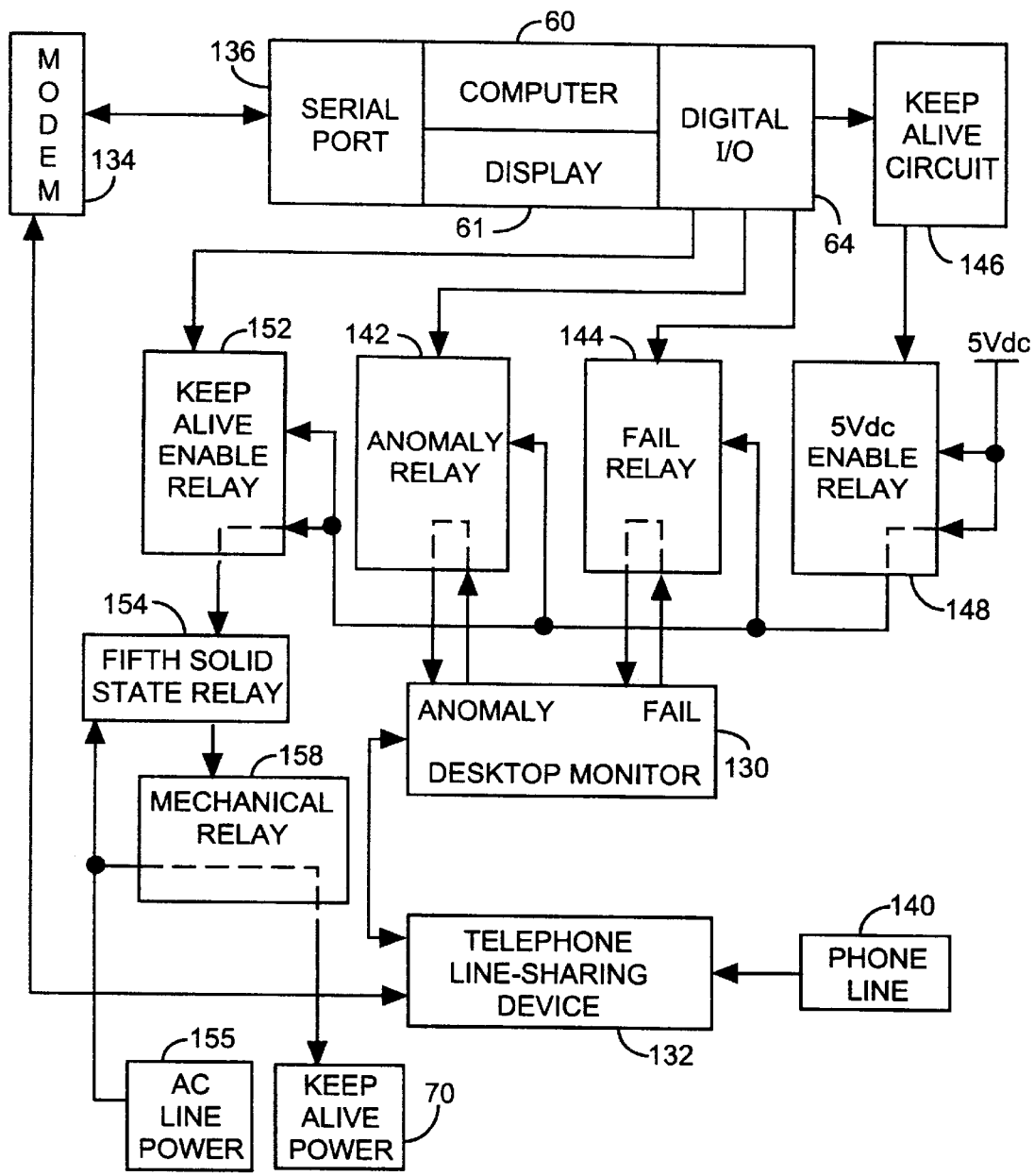
FIG. 5 is a diagram depicting response control.

Referring to all of the Figures, and particularly to FIG. 5, the computer 60 can function as a front-end controller to fully automate the thermal cycling system enabling the system to provide continuous long-term, unattended failsafe thermal cycling. An interactive user interface is visually presented on a computer display 61. A desktop monitoring device 130 is connected to the computer 60 through a telephone line sharing device 132, a modem 134 and a serial port 136 of the computer 60. The desktop monitor 130 can alert a user by communicating to a user through the phone line 140 and can receive inquiries from a user through the phone line 140 and the telephone sharing device 132. The computer display 61 enables a user to view presented cycle indicators and status and enables a user to alter control values without interrupting cycling in progress. The monitor 130 monitors the state of an anomaly relay 142 and a failure relay 144 actuated by respective control signals from the digital I/O 64 indicating a respective anomaly or failure. A keep alive circuit 146 also receiving a control signal from the digital I/O 64 controls a 5 Vdc enable relay 148 for providing keep alive 5 Vdc power from a 5 Vdc reference. The keep alive 5 Vdc power supplies power to the anomaly relay 142, failure relay 144, and a keep alive enable relay 152 that is also controlled by the computer 60 through the digital I/O 64. The keep alive enable relay 152 routes keep alive 5 Vdc power to a fifth solid state relay 154 that is powered by 115 VAC AC line power 155 and controlled by the keep alive 5 VDC power from the relay 152. The fifth relay 154 controls a mechanical relay 158 for coupling the AC line power 155 to keep alive power 70, and for removing power from the keep alive 115 VAC power 70 in the event of a failure. The computer 60, the desktop monitor 130, and computer display 61 function in combination to provide a user communication method for presenting status, for controlling the thermal cycling process and for alerting a user to critical events.

Computer programming enables routine data acquisition, fail-safe thermal cycle control, data archiving, and monitors critical processes for anomalies. A primary function of the thermal cycling system is to ensure the protection of personnel, equipment, and devices 48 under test. The alarm desktop monitor 130 operates independently of the computer 60 and automatically notifies the operator in response to signals initiated by the computer 60 indicating a computer latch-up or loss of power. Remote computer links through a phone line 140 permit the user to modify control parameters and to correct problems from a remote location. These remote links are especially important during the crucial beginning phase of a life test when panel cycling behavior must be fully characterized before the optimum control can be achieved. Specialized program control routines are usually developed for each type of device for specific converging of the operating extreme temperatures, thermal rates and cycle times.

The thermal cycling system is preferably designed to respond to failures by shutting off all external processes and notifying the operator. The keep-alive circuit 146 is used for failure response. The keep alive circuit 146 receives digital pulses from the computer 60 at predetermined time intervals, for example, at least once every thirty seconds to remain enabled. If this does not occur, then a sequence is initiated that removes external power by de-energizing mechanical relay 158. The sequence also triggers an automatic anomaly and failure alert from the desktop monitor 130 by disabling an anomaly relay 142 and a failure relay 144. This failure to provide digital pulses; could be caused by a computer software or hardware latch-up or by unexpected termination of the control program. In addition, the failure response system allows the computer control program to directly trigger an anomaly or failure call-out and to shut down external process power. This occurs automatically as the result of out-of-range readings in critical thermal processes being monitored.

The user communication method not only provides operator notification, but also lets the operator call in to the desktop monitor to hear a status report and listen to the experiment in operation. The telephone line-sharing device 132 automatically routes incoming phone calls to the desktop monitor 130, but diverts remote computer call-ins directly to the modem 134. A terminate and stay resident program running in the background on the host computer permits a similar program running on a remote guest computer to control the host via the modem connection. Extensive on-screen logistics allow the operator to make sound decisions about the operation of the facility, even from an off-site remote computer. The operator can access the computer from any remote computer, scroll through menus without cycle control interruption, and change process control parameters on the fly to optimize cycling performance or to correct for aberrant behavior.

General test logistics, such as the time, date, cycles completed, and a test-file name, are displayed on the main screen of the computer display 61. The test file has a unique time, day and year formatted name. New cycle data is appended to this file every cycle to characterize and archive each cycle's performance. A motor control panel on screen displays the position of the panel 46 and enables manual motor excursion control. The ongoing panel temperatures are displayed, along with the maximum and minimum temperature extremes encountered up to that point during the current cycle. Also shown on the main screen are the maximum and minimum temperatures existing at the moment of the heating and cooling phase transitions for the last cycle. These maximum and minimum temperatures are used by the control code to converge to the mandated target temperature extremes. The panel heating process using the infrared lamp sets 18*a–d* are also depicted showing the immediate output control settings for each lamp set 18*a–d* and the resultant current produced in each set 18*a–d*. The liquid nitrogen canister temperature from thermocouple 58 indicates the fill level of the canister for comparison to a target fill level, and the immediate cycle control mode is displayed indicating either heating, cooling, dwelling, or idling at a predetermined temperature.

There are also auxiliary menu screens to scroll through and view other process indicators or change control parameters, such as the converging temperatures extremes. In addition, a screen recapping the thermal extremes of the last several cycles can be viewed. Both this recap screen and the menus are viewed while the control program is still running in the background. These extensive on-screen logistics provide the operator with sufficient information to make sound decisions concerning the operation of the cycler, even from a remote computer. The operator can access the computer from an off-site computer, scroll through menus without program interruption, and change process control parameters on the fly to optimize cycling performance or correct for aberrant cycler behavior. The computer acquires data such as heating lamp currents, liquid nitrogen cooling canister levels, solar cell panel temperatures, and the panel's position. Using this information for control feedback, the computer outputs proportionate heating power to the lamps, maintains the cooling shroud temperatures, actuates external devices, and commands a microstepping motor to transport the panel between the top and bottom compartments. The computer outputs analog voltages into proportionate solid-state relays to vary the heating lamp power. Digital outputs from the computer trigger solid-state relays to actuate external devices such as gas purge solenoids, liquid nitrogen bellows valves, and fail-safe hardware relays.

The solar cell panel position is constantly examined by the computer, regardless of the cycling mode. During panel positioning the motor excursion is monitored to sense stalls or any motion irregularities, while at all other times the panel is checked to verify proper positioning. Stalls, motion irregularities, and improper panel positions will remove power from the motor controller, and a counterweight will return the panel to the home position in the top chamber, where the lamps are on at low power to keep the panel warm. In the event of any kind of failure, hardware independent of the computer removes power to all external processes, safely terminates the test, and notifies the operator. During the test, data files are generated that provide an archived log of the performance during every cycle. This log includes the maximum and minimum temperatures encountered for each thermocouple for every cycle. User presentations represent the temperature distributions at the heating extreme that are archived for each cycle, along with the maximum and minimum values for the heating and cooling extremes.

In addition, at select cycles, all panel temperatures and dwell phase current test data are captured every few seconds, such as every three seconds, throughout an entire cycle and stored in a file for later plotting and presentation indicating the maximum rate for that particular cycle. It is desirable not only to characterize the thermal cycling for evaluation after cycling, but also to prevent or alert the operator of aberrations during the test. Therefore, the control program checks for anomalies and failures continuously throughout the test. Among the conditions of concern are temperatures out of range, open control thermocouples, excessive thermal rates, extended cycle periods, dwell test voltages or currents out of range, and improper panel positioning.

The code responds to an anomaly by saving the status of all indicators at the time of the occurrence to a dedicated notepad file, and initiating an automatic telephone call-out to alert the operator of the anomaly. The cycling, however, is allowed to continue uninterrupted. In response to circumstances that the program deems to be indicative of a failure, not only is the anomaly response taken, but also the cycling is terminated, and the system assumes a safe idle mode of operation. In the event of catastrophic failures not initiated by the computer such as computer latch-up or power loss, dedicated hardware on uninterruptable power supply back-up power automatically orchestrates a safe shutdown and triggers a telephone call-out. At various times during the life test, and at its completion, the devices may be removed to undergo extensive electrical performance evaluation tests.

Thermal cycling testing is used to attain the thermal cycles corresponding to an operational life span to verify survivability of the device. A cycler can be used to conduct a 25,000 cycle test with typical thermal cycling temperature extremes between +106° C. and −69° C. The cycle periods are extended to avoid exceeding designed safe panel thermal rates. The potential five minute cycling capability of the cyclers may exceed allowable maximum thermal rates in both the cooling and heating phases. The thermal cycler system includes a bifurcated temperature cycling chamber having a top hot compartment for heating and a bottom cold compartment for cooling, with suitable heaters such as lamps, coolers such as liquid nitrogen shrouds, temperature sensors such thermocouples, thermal conducting pressurized gas such as gaseous nitrogen, and transport means for moving a device under test between the two compartments for temperature cycling. The system may be enhanced or modified with in-situ testing and alert communications. This system may be further enhanced or modified by those skilled in the art, but those enhancements and modifications may nonetheless fall within the spirit and scope of the claims that follow.

What is claimed is:

1. A thermal cycling system for repetitively thermal cycling a device, the system comprising,
   a hot compartment for heating the device,
   a first heater for heating the device in the hot compartment,
   a cold compartment for cooling the device,
   a cooler for cooling the device in the cold compartment,
   a second heater for heating the device in the cold compartment for reducing thermal gradients across the device during cooling,
   an aperture between the hot compartment and the cold compartment, and
   a motor for repetitively transporting the device between the hot and cold compartments.

2. A thermal cycling system of claim 1 further comprising,
   a gas source for supplying a pressurized gas, and
   the hot compartment and cold compartment constitute a bifurcated chamber filled with the pressured gas for removing moisture from the bifurcated chamber.

3. A thermal cycling system for repetitively thermal cycling a device, the system comprising,
   a plurality of temperature sensors for sensing temperatures across the device,
   a hot compartment for heating the device,
   a plurality of heaters for heating the device in the hot compartment to a hot temperature,
   a cold compartment for cooling the device,
   a cooler for cooling the cold compartment to a cold temperature,
   a heater disposed under the device for heating the device in the cold compartment for reducing thermal gradients across the device during cooling,
   an aperture between the hot compartment and the cold compartment,
   a motor for repetitively transporting the device between the hot and cold compartment, and
   a controller for sensing the temperatures and controlling the heaters to a predetermined hot temperature when the device is in the hot compartment and for controlling the cooler to a predetermined cold temperature when the device is in the cold compartment.

4. The system of claim 3 further comprising,
   electrical connection from the controller to the device for electrical testing the device during temperature cycling of the device.

5. A thermal cycling system of claim 3 further comprising,
   a gas source for supplying pressurized gas, and the hot compartment and the cold compartment constituting a bifurcated chamber filled with the pressurized gas for removing moisture in the bifurcated chamber.

6. The thermal cycling system of claim 3, wherein,
   the controller senses a hot temperature extreme of the sensed temperature across the device when in the hot compartment to determine a temperature difference between the hot temperature extreme to a predetermined hot target temperature to control the plurality of heaters to heat the device in a next cycle to minimize the temperature difference in the next cycle.

7. The thermal cycling system of claim 3, wherein,
   the controller controls the plurality of heaters to minimize a difference in the sensed temperature across the device when in the hot compartment.

8. The thermal cycling system of claim 3, wherein,
   the controller senses a hot temperature extreme of the sensed temperature across the device when in the hot compartment to determine a temperature difference between the temperature extreme to a predetermined hot target temperature to control the plurality of heaters to heat the device in a next cycle to minimize the temperature difference in the next cycle, and
   the controller controls the plurality of heaters to minimize a difference in the sensed temperature across the device at the temperature extreme.

9. The thermal cycling system of claim 3 further comprises,
   said heater in the cold compartment controlled by the controller for warming the device when being cooled in the cold compartment, the controller controls the cooler to cool the device in the cold compartment to a predetermined cold target temperature, the controller senses a cold temperature extreme of the sensed temperature across the device when in the cold compartment to determine a temperature difference between the cold temperature extreme to a predetermined cold target temperature to control the heater in the cold compartment to warm the device in a next cycle to minimize the temperature difference in the next cycle.

10. The system of claim 1 further comprising,
    a plurality of temperature sensors disposed across the device for sensing the temperature of the device and for sensing temperature gradients across the device during cooling.

11. The system of claim 3 further comprising,
    a plurality of temperature sensors disposed across the device for sensing the temperature of the device and for sensing temperature gradients across the device during cooling.

12. The thermal cycling system of claim 10 further comprising,
    said heater in the cold compartment controlled by a controller for warming the device when being cooled in the cold compartment, the controller controls the cooler to cool the device in the cold compartment to a predetermined cold target temperature, the controller senses a cold temperature extreme of the sensed temperature across the device when in the cold compartment to determine a temperature difference between the cold temperature extreme to a predetermined cold target temperature to control the heater in the cold compartment to warm the device in a next cycle to minimize the temperature difference in the next cycle.

* * * * *